United States Patent
Yamaoka

(10) Patent No.: US 10,101,302 B2
(45) Date of Patent: Oct. 16, 2018

(54) ULTRASONIC FLAW DETECTOR

(71) Applicant: KAWASAKI JUKOGYO KABUSHIKI KAISHA, Kobe-shi, Hyogo (JP)

(72) Inventor: Toshihiro Yamaoka, Nagoya (JP)

(73) Assignee: KAWASAKI JUKOGYO KABUSHIKI KAISHA, Kobe-shi (JP)

( * ) Notice: Subject to any disclaimer, the term of this patent is extended or adjusted under 35 U.S.C. 154(b) by 153 days.

(21) Appl. No.: 14/915,386

(22) PCT Filed: Aug. 27, 2014

(86) PCT No.: PCT/JP2014/004407
§ 371 (c)(1),
(2) Date: Feb. 29, 2016

(87) PCT Pub. No.: WO2015/029429
PCT Pub. Date: Mar. 5, 2015

(65) Prior Publication Data
US 2016/0209373 A1     Jul. 21, 2016

(30) Foreign Application Priority Data
Aug. 30, 2013    (JP) .................................. 2013-179633

(51) Int. Cl.
*G01N 29/22*    (2006.01)
*G01N 29/04*    (2006.01)
(Continued)

(52) U.S. Cl.
CPC ........... *G01N 29/225* (2013.01); *G01N 29/04* (2013.01); *G01N 29/043* (2013.01);
(Continued)

(58) Field of Classification Search
CPC .... G01N 29/225; G01N 29/32; G01N 29/043; G01N 29/265; G01N 29/30; G01N 29/04;
(Continued)

(56) References Cited

U.S. PATENT DOCUMENTS

| 4,848,159 A | 7/1989 | Kennedy et al. |
| 5,372,043 A * | 12/1994 | Speight, II ............. G01N 29/26 |
| | | 73/619 |

(Continued)

FOREIGN PATENT DOCUMENTS

| EP | 0 289 207 A2 | 11/1988 |
| JP | H06-27093 A | 2/1994 |

(Continued)

OTHER PUBLICATIONS

Mar. 7, 2017 Extended Search Report issued in European Patent Application No. 14839898.5.
(Continued)

*Primary Examiner* — Hezron E Williams
*Assistant Examiner* — Xin Zhong
(74) *Attorney, Agent, or Firm* — Oliff PLC

(57) ABSTRACT

An ultrasonic flaw detector includes: a flaw detection head including a probe that transmits an ultrasonic wave to an inspection object formed by a composite member and receives the ultrasonic wave that has reflected on the inspection object; a moving mechanism, which causes the flaw detection head to perform scanning; and a support mechanism disposed such that the support mechanism comes into contact with a lower surface of the inspection object, the support mechanism supporting the inspection object. The support mechanism is configured to come into contact with the inspection object over a predetermined area such that a waveform of the ultrasonic wave that has reflected on a position where the support mechanism is in contact with the (Continued)

inspection object and that is received by the probe is within a noise level.

11 Claims, 4 Drawing Sheets

(51) Int. Cl.
 *G01N 29/30* (2006.01)
 *G01N 29/265* (2006.01)
 *G01N 29/32* (2006.01)
(52) U.S. Cl.
 CPC ........... *G01N 29/265* (2013.01); *G01N 29/30* (2013.01); *G01N 29/32* (2013.01); *G01N 2291/0231* (2013.01); *G01N 2291/044* (2013.01); *G01N 2291/2632* (2013.01); *G01N 2291/2638* (2013.01); *G01N 2291/2694* (2013.01)
(58) Field of Classification Search
 CPC ..... G01N 2291/2694; G01N 2291/044; G01N 2291/2632; G01N 2291/0231; G01N 2291/2638
 See application file for complete search history.

(56) References Cited

U.S. PATENT DOCUMENTS

| | | | | |
|---|---|---|---|---|
| 2009/0049920 A1* | 2/2009 | Young | ............... | G01N 29/07 73/649 |
| 2014/0026668 A1* | 1/2014 | Gayle | ............ | G01N 29/043 73/632 |

FOREIGN PATENT DOCUMENTS

| | | |
|---|---|---|
| JP | H07-146279 A | 6/1995 |
| JP | H09-101288 A | 4/1997 |
| JP | 2002-031623 A | 1/2002 |
| JP | 2007-147513 A | 6/2007 |
| JP | 2009-236808 A | 10/2009 |
| JP | 2011-099810 A | 5/2011 |
| JP | 2013-007686 A | 1/2013 |

OTHER PUBLICATIONS

Oct. 28, 2014 Search Report issued in International Patent Application No. PCT/JP2014/004407.
Oct. 28, 2014 Written Opinion issued in International Patent Application No. PCT/JP2014/004407.
Mar. 1, 2016 International Preliminary Report on Patentability issued in International Patent Application No. PCT/JP2014/004407.

* cited by examiner

ULTRASONIC FLAW DETECTOR

TECHNICAL FIELD

The present invention relates to an ultrasonic flaw detector and particularly relates to an ultrasonic flaw detector that performs inspection of a composite component.

BACKGROUND ART

Defect inspection of a composite component is performed with use of an ultrasonic flaw detector by a transmission method or a reflection method. The inspection by the transmission method is performed in the following manner: receive an ultrasonic wave that has been transmitted through a composite component; and determine based on the energy of the received ultrasonic wave whether or not the composite component has a defect. On the other hand, the inspection by the reflection method is performed in the following manner: receive an ultrasonic wave that has reflected on a composite component; and determine based on the energy of the received ultrasonic wave whether or not the composite component has a defect.

Among such ultrasonic flaw detectors, there is a known ultrasonic flaw detector that is intended to inspect a plurality of inspection objects (composite components) (see Patent Literature 1 for example). The ultrasonic flaw detector disclosed in Patent Literature 1 includes a plurality of pallets. Inspection objects are disposed for the respective pallets. The inspection objects are supported by a plurality of wires provided on the pallets. By conveying the pallets, a work time required for flaw detection inspection of the plurality of inspection objects is reduced.

CITATION LIST

Patent Literature

PTL 1: Japanese Laid-Open Patent Application Publication No. 2011-99810

SUMMARY OF INVENTION

Technical Problem

However, in the ultrasonic flaw detector disclosed in Patent Literature 1, metal wires are used. Accordingly, at portions of the inspection objects (composite components), the portions being in contact with the wires, the reflectance of the ultrasonic wave changes due to the wires. This may result in imprecise inspection.

Moreover, in order to perform precise inspection, it is necessary to move these portions of the inspection objects from the contacting wires and re-perform flaw detection inspection on these portions. Thus, there is at problem in that the flaw detection inspection is time-consuming.

Furthermore, since the inspection objects are supported by the wires, in a case where a flaw detection head scans each inspection object in a manner to contact the inspection object (i.e., in a manner to press on the inspection object), if adjoining wires are spaced apart from each other by a great distance, the inspection object may bend or warp, and thereby the distance between the inspection object and a probe cannot be kept constant. This may result in imprecise inspection.

The present invention solves the above conventional problems. An object of the present invention is to provide an ultrasonic flaw detector that performs flaw detection inspection of an inspection object while supporting the inspection object by a support mechanism and that is capable of reducing an increase or decrease in the reflectance of an ultrasonic wave due to the support mechanism, reducing the work time of the inspection of the inspection object, and performing the inspection of the inspection object precisely.

Solution to Problem

In order to solve the above-described conventional problems, an ultrasonic flaw detector according to the present invention includes: a flaw detection head including a probe that transmits an ultrasonic wave to an inspection object formed by a composite member and receives the ultrasonic wave that has reflected on the inspection object; a moving mechanism that causes the flaw detection head to perform scanning; and a support mechanism disposed such that the support mechanism comes into contact with a lower surface of the inspection object, the support mechanism supporting the inspection object. The support mechanism is configured to come into contact with the inspection object over a predetermined area such that a waveform of the ultrasonic wave that has reflected on a position where the support mechanism is in contact with the inspection object and that is received by the probe is within a noise level.

This configuration makes it possible to, while supporting the inspection object formed by the composite member by the support mechanism, reduce an increase or decrease in the reflectance of the ultrasonic wave due to the support mechanism and perform inspection of the inspection object precisely.

Advantageous Effects of Invention

The ultrasonic flaw detector according to the present invention makes it possible to, while supporting the inspection object formed by the composite member by the support mechanism, reduce an increase or decrease in the reflectance of the ultrasonic wave due to the support mechanism, reduce the work time of the inspection of the inspection object, and perform the inspection precisely.

DESCRIPTION OF EMBODIMENTS (Fundamental Findings)

The inventors of the present invention conducted diligent studies aiming to perform ultrasonic flaw detection inspection of an inspection object formed by a composite member in a simpler manner than conventional art. As a result of the studies, the inventors have obtained the following findings. Specifically, a probe is configured to transmit/receive an ultrasonic wave over a predetermined range (area). An inspection object formed by a composite member has a non-uniform internal structure. For this reason, the probe receives not only the ultrasonic wave that has reflected on the front surface of the inspection object and the ultrasonic wave that has reflected on the back surface of the inspection object but also material noise, i.e., the ultrasonic wave that has reflected on internal components of the inspection object.

Meanwhile, an ultrasonic flaw detection inspection apparatus receives electrical noise from various internal parts, such as from the inside of its devices or from probe cables.

Figure 4:
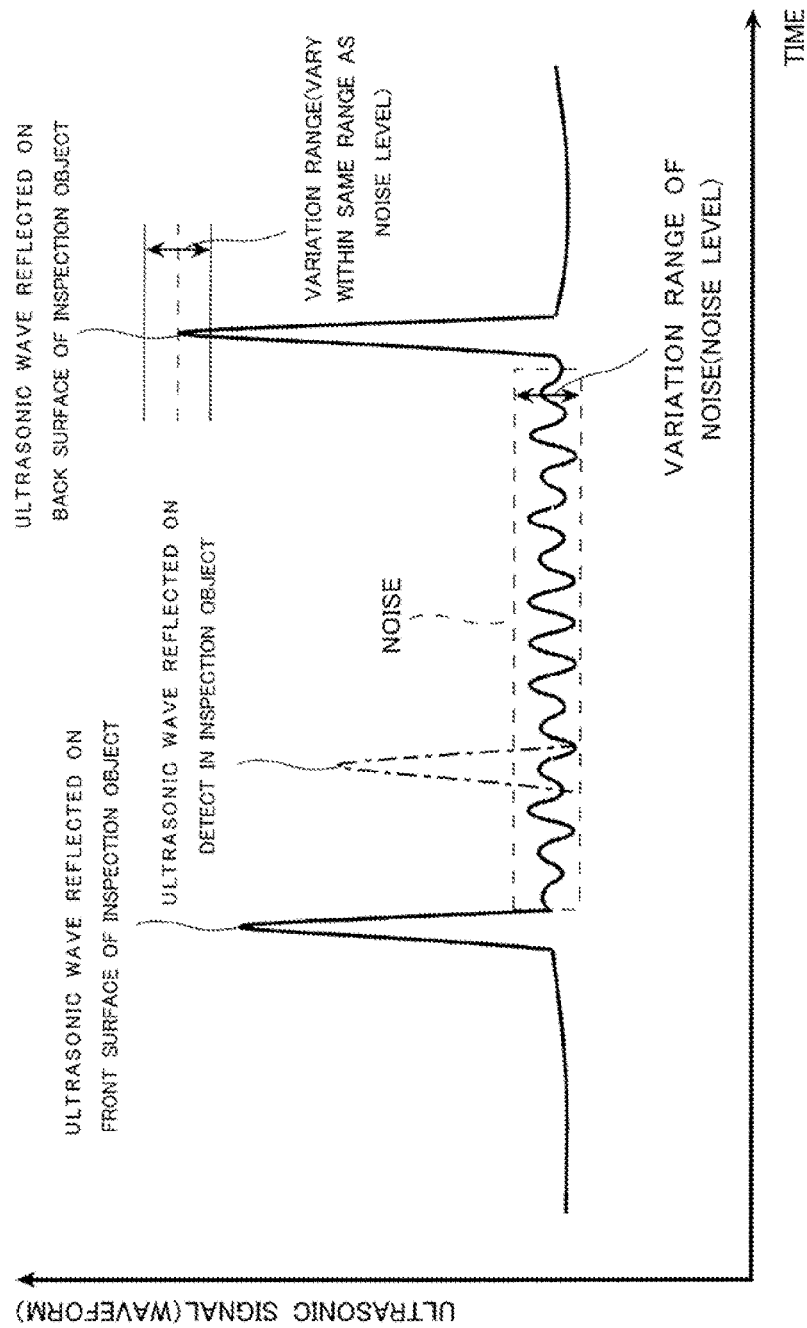
FIG. 4 is a graph showing one example of the results of ultrasonic flaw detection of an inspection object formed by a composite member.

Then, as shown in FIG. 4, the ultrasonic wave that has reflected on the internal components of the inspection object (i.e., the material noise) and the noise that has occurred inside the apparatus (i.e., the electrical noise) are combined together and appear as a minute waveform (noise). For this reason, the ultrasonic wave that has reflected on the back surface of the inspection object and that is received by the probe varies depending on the noise. It should be noted that the noise herein is, as shown in FIG. 4, a waveform (of the ultrasonic wave) that is, in a case where there is a defect inside the inspection object, sufficiently smaller than the magnitude (waveform) of the ultrasonic wave that has reflected on the defect, i.e., a waveform of such a level that the inspection can be performed with a sufficiently high SN ratio (signal-noise ratio).

In view of the above, the inventors of the present invention have found out that if the reflectance of the ultrasonic wave increasing or decreasing due to the support mechanism supporting the inspection object is in a proportion that is within the range of the variation of the noise, i.e., noise-level reflectance, then the SN ratio is kept within such a range that the inspection will not be hindered, and even if the inspection of the inspection object is performed in a state where the inspection object is supported by the support mechanism, the inspection will not be hindered. Based on these findings, the inventors have arrived at the present invention. In other words, the inventors have found out that hindrance to the inspection of the inspection object can be prevented by suppressing the noise due to the support mechanism at portions of the inspection object that are supported by the support mechanism to a degree that is substantially the same as the degree of the variation of the ultrasonic wave that has been transmitted through the inside the inspection object and reached the back surface of the inspection object, and thus the inventors have arrived at the present invention.

It should be noted that since the electrical noise can be almost entirely removed by taking various measures in the ultrasonic flaw detection inspection apparatus, the aforementioned noise may be treated as the material noise.

Hereinafter, preferred embodiments of the present invention are described with reference to the drawings. In the drawings, the same or corresponding components are denoted by the same reference signs, and repeating the same descriptions is avoided. In the drawings, only the components necessary for describing the present invention may be shown, and the other components may be omitted. Further, the present invention is not limited to the embodiments described below.

Embodiment 1

An ultrasonic flaw detector according to Embodiment 1 includes: a flaw detection head including a probe that transmits an ultrasonic wave to an inspection object formed by a composite member and receives the ultrasonic wave that has reflected on the inspection object; a moving mechanism that causes the flaw detection head to perform scanning; and a support mechanism disposed such that the support mechanism comes into contact with a lower surface of the inspection object, the support mechanism supporting the inspection object. The support mechanism is configured to come into contact with the inspection object over a predetermined area such that a waveform of the ultrasonic wave that has reflected on a position where the support mechanism is in contact with the inspection object and that is received by the probe is within a noise level.

This configuration makes it possible to, while supporting the inspection object formed by the composite member by the support mechanism, reduce an increase or decrease in the reflectance of the ultrasonic wave due to the support mechanism and perform inspection of the inspection object precisely.

In the ultrasonic flaw detector according to Embodiment 1, the support mechanism may include a base; and a plurality of protruding portions provided upright on the base and configured such that distal ends of the respective protruding portions come into contact with the lower surface of the inspection object.

In the ultrasonic flaw detector according to Embodiment 1, each of the distal ends of the protruding portions may be formed in a tapered shape.

In the ultrasonic flaw detector according to Embodiment 1, the support mechanism may further include a rotating portion that causes a state of the protruding portions to change between an upright state where the protruding portions are upright and a laid-down state where the protruding portions are laid down.

The ultrasonic flaw detector according to Embodiment 1 may further include a retaining mechanism that retains the inspection object.

In the ultrasonic flaw detector according to Embodiment 1, the retaining mechanism may include a pair of arm members, and may be configured to retain the inspection object by sandwiching, by the pair of arm members, both ends of the inspection object that are not subjected to the scanning.

Hereinafter, one example of the ultrasonic flaw detector according to Embodiment 1 is described in detail with reference to the drawings.

[Configuration of Ultrasonic Flaw Detector]

Figure 1:
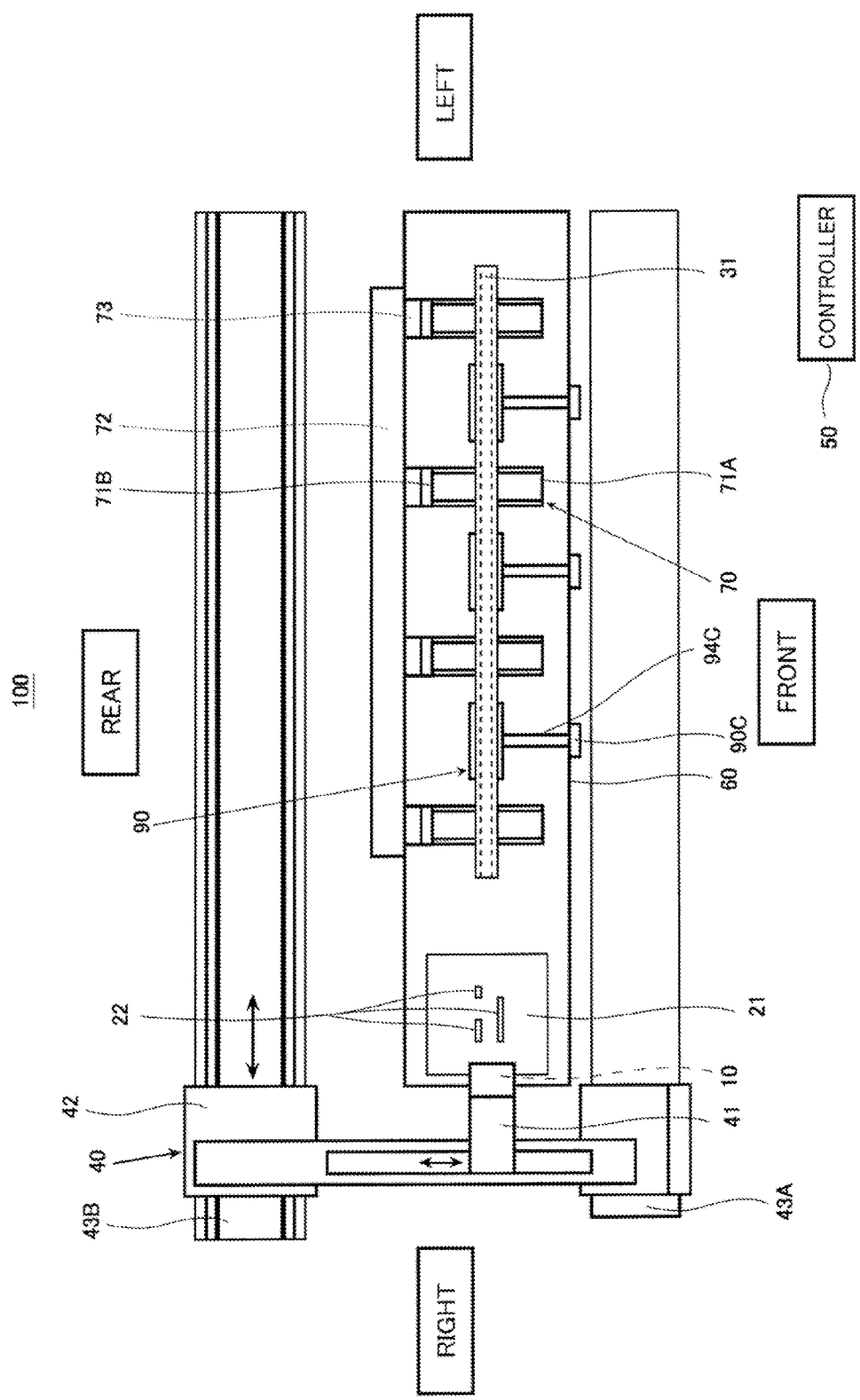
FIG. 1 is a schematic diagram showing a schematic configuration of an ultrasonic flaw detector according to Embodiment 1.
Figure 2:
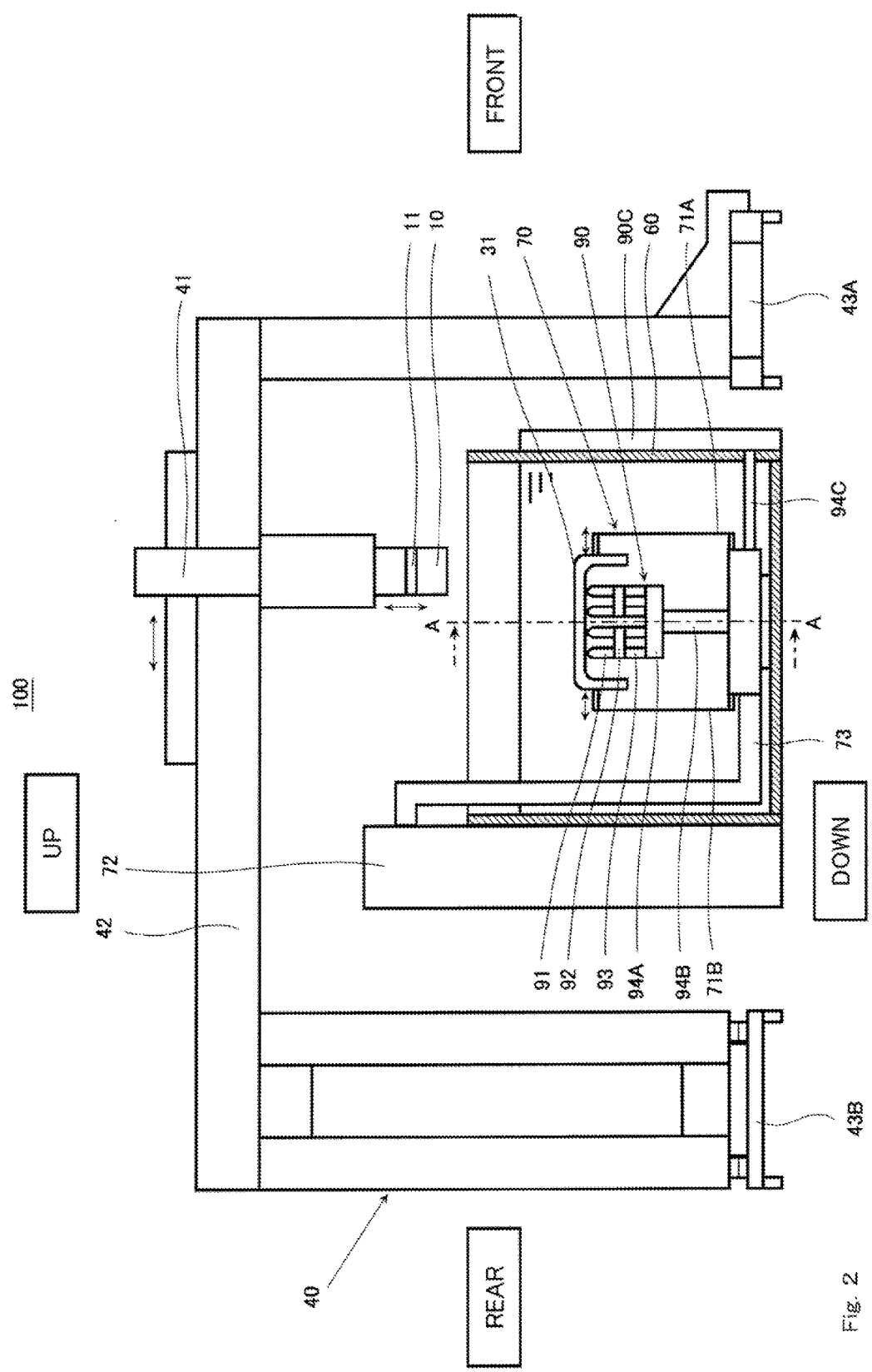
FIG. 2 is a schematic diagram showing a schematic configuration of the ultrasonic flaw detector according to Embodiment 1.
Figure 3:
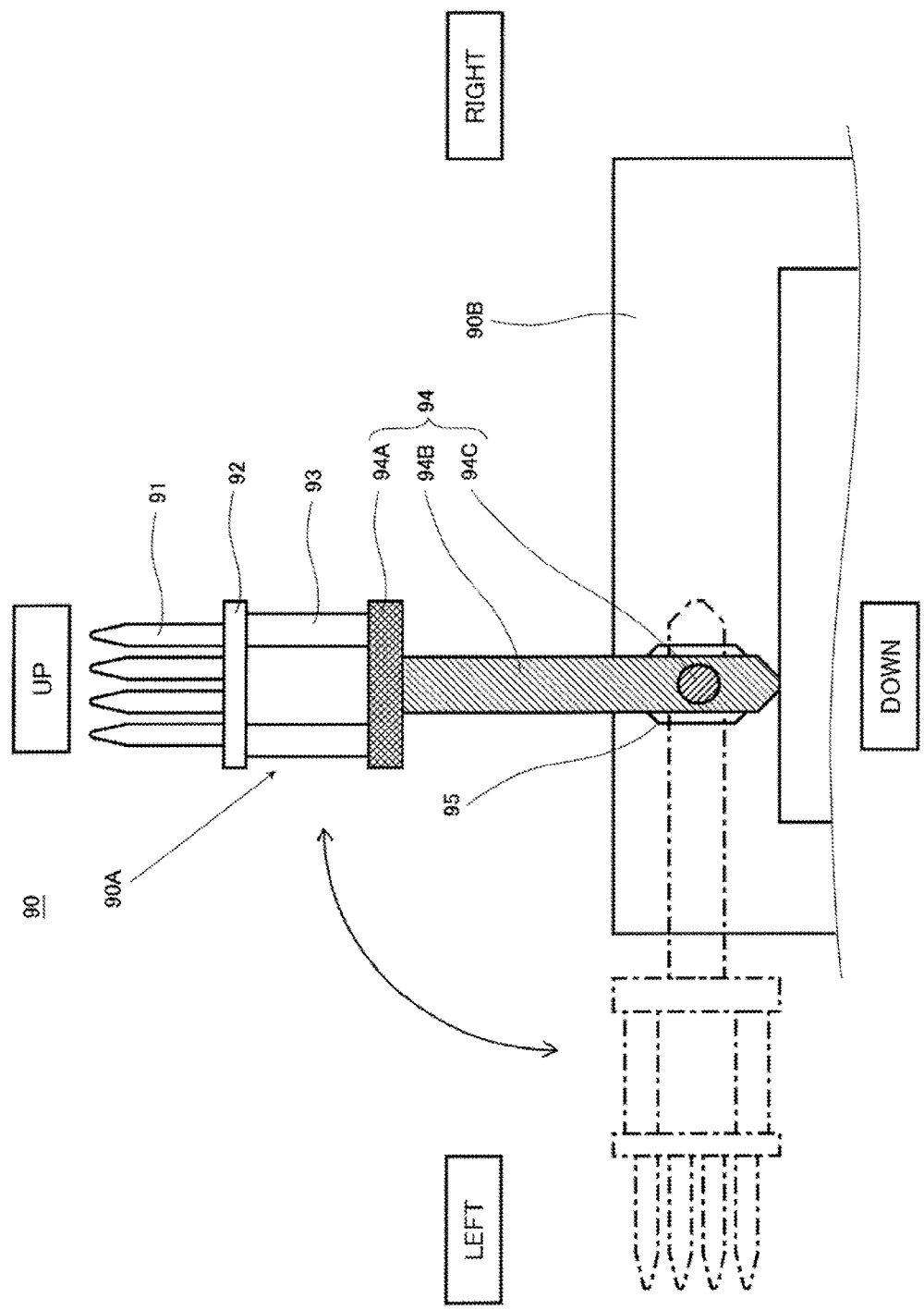
FIG. 3 is a sectional view of a support mechanism of the ultrasonic flaw detector taken along a line A-A shown in FIG. 2.

FIG. 1 and FIG. 2 are schematic diagrams each showing a schematic configuration of the ultrasonic flaw detector according to Embodiment 1. FIG. 1 is a schematic diagram showing a top view of the ultrasonic flaw detector, and FIG. 2 is a schematic diagram showing a front view of the ultrasonic flaw detector. FIG. 3 is a sectional view of a support mechanism of the ultrasonic flaw detector taken along a line A-A shown in FIG. 2.

It should be noted that, in FIG. 1, the front-rear direction and the right-left direction of the ultrasonic flaw detector are the front-rear direction and the right-left direction shown in FIG. 1. Similarly, in FIG. 2, the up-down direction and the front-rear direction of the ultrasonic flaw detector the up-down direction and the right-left direction shown in FIG. 2. FIG. 2 shows the internal configuration of a container for the purpose of showing the shape of each device provided inside the container. In FIG. 3, the ultrasonic flaw detector is partially omitted, and a state where protruding portions are laid down is indicated by one-dot chain lines.

As shown in FIG. 1 and FIG. 2, an ultrasonic flaw detector 100 according to Embodiment 1 includes: a flaw detection head 10 including a sensor (a probe) that inspects an inspection object 31; a moving mechanism 40; a controller a container 60; and a support mechanism 90.

Specifically, the container 60 is formed in the shape of a rectangular parallelepiped, and is disposed such that the longitudinal direction of the container 60 coincides with the right-left direction. The upper part of the container 60 is open. The inspection object 31 and the support mechanism 90 are disposed in the internal space of the container 60. The flaw detection head 10 is retained by the moving mechanism 40, and the moving mechanism 40 is configured to cause the flaw detection head 10 scan the inspection object 31.

Water is stored in the internal space of the container 60, and the inspection object 31 is supported by the support mechanism 90. The inspection object 31 herein is long in the right-left direction and has a U-shaped cross section. The inspection object 31 is disposed such that its curved portion is positioned upward (see FIG. 2).

Although Embodiment 1 adopts a configuration in which water is stored in the internal space of the container 60, the configuration is not thus limited. Alternatively, a configuration in which no water is stored in the internal space of the container 60, i.e., a configuration in which the internal space of the container 60 is filled with air, may be adopted. Also, in Embodiment 1, the inspection object 31 may be, for example, an aircraft component that is formed by composite members. The cross-sectional shape of the inspection object 31 is not limited to a U-shape, but may be any shape among various shapes including a T-shape, I-shape, L-shape, etc.

A calibration standard sample 21 is disposed at the right-side end in the container 60. Artificial defects 22 necessary for performing calibration of the flaw detection head 10 are formed in the calibration standard sample 21. Although in Embodiment 1 the calibration standard sample 21 is disposed at the right-side end in the container 60, the position at which the calibration standard sample 21 is disposed is not thus limited. Alternatively, the calibration standard sample 21 may be disposed at the left-side end in the container 60 or may be disposed at an upper position in the container 60. Further alternatively, calibration standard samples 21 may be disposed at both ends in the container 60 in the right-left direction, respectively.

At the front and rear of the container 60, a guide member 43A and a guide member 43B are disposed, respectively. The guide member 43A and the guide member 43B are formed to extend in the longitudinal direction of the container 60 (i.e., in the right-left direction). Specifically, the guide member 43A and the guide member 43B are disposed such that, when seen in the up-don direction of the ultrasonic flaw detector 100, the guide member 43A and the guide member 43B are parallel to each other with the container 60 positioned in between them.

The moving mechanism 40 is placed on the guide member 43A and the guide member 43B, and is configured to move in the right-left direction along the guide member 43A and the guide member 43B.

The ultrasonic flaw detector 100 according to Embodiment 1 includes a retaining mechanism 70 for retaining the inspection object 31 during flaw detection. The retaining mechanism 70 is disposed in the internal space of the container 60.

The retaining mechanism 70 includes pairs of arm members 71A and 71B (in this example, four pairs of arm members 71A and 71B). The retaining mechanism 70 retains the inspection object 31 by sandwiching portions of the inspection object 31 with use of the arm members 71A and 71B, the portions being not subjected to the scanning by the flaw detection head 10 (in this example, the portions are both ends of the inspection object 31 (specifically, both ends in the front-rear direction (width direction)).

Next, devices forming the ultrasonic flaw detector 100 according to Embodiment 1 are further described in detail with reference to FIG. 1 to FIG. 3.

[Configuration of Moving Mechanism]

As shown in FIG. 1 and FIG. 2, the moving mechanism 40 includes a moving part 41 and a gantry part 42, and is disposed at the right-side end of the ultrasonic flaw detector 100. The moving mechanism 40 includes known actuators such as motors, gears, pistons, or cylinders. The moving mechanism 40 is configured to cause, by use of the actuators, the flaw detection head 10 to move and/or rotate in the front-rear, right-left, and up-down directions. That is, the moving mechanism 40 is configured to cause the flaw detection head 10 to move triaxially and/or rotate triaxially. It should be noted that the actuators of the moving mechanism 40 may be in any form, so long as the actuators can cause the flaw detection head 10 to move and/or rotate in the front-rear, right-left, and tip-down directions.

The gantry part 42 is formed to be arch-shaped such that the gantry part 42 straddles over the container 60 when seen in the right-left direction. Specifically, the gantry part 42 includes a pair of leg portions provided upright at the front and rear of the container 60 and a bridging portion connecting between the upper ends of the leg portions. The base ends of the pair of leg portions of the gantry part 42 are in contact with the upper ends of the guide members 43A and 43B, respectively. Actuators, such as motors, are provided at the base ends of the leg portions oldie gantry part 42 (not shown) so that the gantry part 42 can move along the guide members 43A and 43B.

The moving mechanism 40 can move linearly in the right-left direction by moving along the guide members 43A and 43B, thereby moving the flaw detection head 10 in the right-left direction. It should be noted that one of or both the guide member 43A and the guide member 43B may be eliminated, so long as the moving mechanism 40 can move linearly in the right-left direction (i.e., in a non-serpentine manner).

The bridging portion of the gantry part 42 is provided with: the moving part 41 extending downward; and an actuator such as a motor (not shown) that allows the moving pan 41 to move in the front-rear direction. The moving part 41 is provided with an actuator such as a motor that allows the flaw detection head 10 to advance or retreat in the up-down direction. Accordingly, the flaw detection head 10 can move in the front-rear or up-down direction.

[Configuration of Flaw Detection Head]

As shown in FIG. 2, the flaw detection head 10 is mounted to the moving part 41 of the moving mechanism 40 via a mounting portion 11. The flaw detection head 10 includes a probe. The probe herein is configured to transmit an ultrasonic wave and receive the ultrasonic wave that has reflected on the inspection object 31.

The flaw detection head 10 is roughly categorized into a type configured to perform ultrasonic flaw detection of a flat portion of the inspection object 31 and a type configured to perform ultrasonic flaw detection of a curved portion of the inspection object 31. The flaw detection head of the type that performs flaw detection of a flat portion of the inspection object 31 is further categorized into a type with a wide flaw detection range and a type with a narrow flaw detection range. The flaw detection head of the type that performs flaw detection of a curved portion of the inspection object 31 is further categorized into a type that scans the inner surface side of the inspection object 31 and a type that scans the outer surface side of the inspection object 31.

The ultrasonic flaw detector 100 according to Embodiment 1 is configured to change the flaw detection head 10 as necessary in accordance with a portion to be inspected of the inspection object 31. It should be noted that a plurality of types of flaw detection heads 10 may be mounted to the moving mechanism 40, and the flaw detection head to use may be changed as necessary in accordance with a portion to be inspected of the inspection object 31.

[Configuration of Retaining Mechanism]

The retaining mechanism 70 includes: the pairs of arm members 71A and 71B; a driving unit 72, which accommodates actuators such as motors (not shown) in its casing; a connection part 73, which connects the arm members 71A and 71B and the driving unit 72. The driving unit 72 is configured to move the connection part 73 in the up-down direction and also drive a belt mechanism and so forth described below.

The arm members 71A and the arm members 71B herein are each formed to be U-shaped, and are disposed such that the arm members 71A and the arm members 71B face each other with the driving unit 72 positioned in between them. To be more specific, the front-side arm members 71A are each formed to have a U shape that is open to the rear side, and the right-side arm members 71B are each formed to have a U shape that is open to the front side.

The arm members 71A and the arm members 71B are arranged such that their openings face each other. One of the distal ends (the lower end) of each of the arm members 71A and the arm members 71B is connected to one end of the connection part 73. The other end of the connection part 73 is connected to the actuators inside the driving unit 72.

The connection part 73 includes: a duct extending from the driving unit 72 to the inner bottom of the container 60; and a power transmission mechanism (e.g., a belt mechanism; not shown) accommodated in the duct. The proximal end of the power transmission mechanism is connected to the actuators of the driving unit 72, and the distal end of the power transmission mechanism is connected to the lower end of each of the arm members 71A and 71B via a converter that accommodates a rack, pinion, etc. By operating the power transmission mechanism, the arm members 71A and 71B can be caused to advance or retreat (i.e., move closer to or move away from each other) in the front-rear direction.

Accordingly, by bringing the other distal end (the upper end) of each of the arm members 71A and the arm members 71B into contact with the inspection object 31, the inspection object 31 can be retained. Also, by moving the other distal end of each of the arm members 71A and the arm members 71B away from the inspection object 31, the inspection object 31 can be released from the retained state.

It should be noted that the actuators of the retaining mechanism 70 may be in any form, so long as the actuators can cause the arm members 71A and the arm members 71B to advance or retreat in the front-rear and up-down directions.

[Configuration of Support Mechanism]

As shown in FIG. 1 to FIG. 3, the support mechanism 90 includes a supporting member 90A, a base member 90B, and a driver 90C. The supporting member 90A is mounted to the base member 90B, and is configured to be driven by the driver 90C to rotate such that the state of the supporting member 90A is changed between an upright state and a laid-down state. The base member 90B is a support base that is long in the right-left direction, and is set in the internal space of the container 60. The driver 90C herein is disposed outside the container 60.

The driver 90C includes known actuators such as stepping motors, gears, pistons, or cylinders. The driver 90C is configured to cause the supporting member 90A to rotate by use of the actuators.

The supporting member 90A includes protruding portions 91, bases 92, supports 93, and a rotating portion 94. The rotating portion 94 includes a lower base 94A, a rod 94B, and a shaft 94C. The shall 94C is disposed such that its central axis is positioned to extend in the front-rear direction, and is rotatably supported by a bearing 95 provided in the base member 90B. The rear end of the shaft 94C is connected to the driver 90C.

A through-hole is formed in one end of the rod 94B. The shaft 94C is fitted in the through-hole. Accordingly, the rod 94B can rotate in accordance with rotation of the shaft 94C.

The plate-shaped lower base 94A is provided on the other end of the rod 94B. The lower base 94A herein is formed in a rectangular shape. The other end of the rod 94B is connected to one main surface of the lower base 94A. The proximal end of each of the plate-shaped supports 93 is connected to the other main surface of the lower base 94A. To be more specific, the supports 93 are provided upright on the other main surface of the lower base 94A such that, when seen in the right-left direction, four supports 93 are parallel to one another (such that the four supports 93 are arranged side by side) (see FIG. 2). It should be noted that openings are formed in main surfaces of the supports 93.

Each pair of adjoining supports 93 (a pair of supports 93 positioned at the front side and a pair of supports 93 positioned at the rear side) is formed such that a plate-shaped base 92 extends over the distal ends of the adjoining supports 93 (such that one main surface of the base 92 is connected to the distal ends of the adjoining supports 93). In other words, each base 92 is supported by a corresponding pair of supports 93. The bases 92 herein are each formed in a rectangular shape. It should be noted that the supports 93 may each be plate-shaped or pillar-shaped, so long as the supports 93 can support the bases 92.

On the other main surface of each base 92, for example, eight (2×4) protruding portions 91 are provided upright such that, when seen in the right-left direction (or from-rear direction), the protruding portions 91 are parallel to one another (such that the protruding portions 91 are arranged side by side) (see FIG. 2 and FIG. 3). Although in Embodiment 1 the protruding portions 91 are provided parallel to one another, the arrangement of the protruding portions 91 is not limited to parallel arrangement. The positions at which the protruding portions 91 are arranged are not particularly limited, so long as the ultrasonic wave received by the probe at these positions is a noise-level ultrasonic wave. For example, the protruding portions 91 may be arranged in a staggered manner when seen in the up-down direction.

Each protruding portion 91 is rod-shaped, and the distal end thereof has a tapered shape. The protruding portion 91 may be formed of a resin (e.g., polyacetal). A part of the protruding portion 91, the part coming into contact with the inspection object 31 (i.e., the distal end of the protruding portion 91), may be formed to have a flat surface or may be arc-shaped, so long as the protruding portion 91 will not damage the surface of the inspection object 31.

The total number of protruding portions 91 arranged in the ultrasonic flaw detector 100, the arrangement density of the protruding portions 91, and the area of the distal ends of the protruding portions 91 are suitably set in advance through an experiment or the like in accordance with, for example, the detection sensitivity of the probe and the material, weight, surface structure, and the density of the inspection object 31. That is, the total number of protruding portions 91 arranged in the ultrasonic flaw detector 100 and the area of the distal ends of the protruding portions 91 are suitably set so that the ultrasonic wave reflectance increasing or decreasing due to the support mechanism 90 will be in a noise-level proportion.

In other words, the total number of protruding portions 91 and the area of the distal ends of the protruding portions 91 are set so that the result of performing ultrasonic flaw detection inspection on a region of the inspection object 31, the region being not supported by the support mechanism 90, and the result of performing ultrasonic flaw detection inspection on a region of the inspection object 31, the region being supported by the support mechanism 90, will be the same.

The "region of the inspection object 31, the region being supported by the support mechanism 90" herein means a part of a region (area) of the inspection object 31, the region being subjected to the flaw detection by the probe, in which part not only portions of the inspection object 31, the portions being in contact with the protruding portions 91, but also portions of the inspection object 31, the portions being not in contact with the protruding portions 91, exist. Also, the wording "will be the same" does not mean being completely the same, but means that the discrepancy between the inspection result in the former case and the inspection result in the latter case is a noise-level discrepancy (i.e., the SN ratio is kept within such a range that the inspection will not be hindered).

The controller 50 controls the driver 90C to drive the supporting member 90A such that the state of the supporting member 90A is changed between the upright state where the protruding portions 91 are upright (a state where the protruding portions 91 can come into contact with the lower surface of the inspection object 31; the stale indicated by solid lines in FIG. 3) and the laid-down state where the protruding portions 91 are laid down (indicated by one-dot chain lines in FIG. 3).

It should be noted that the controller 50 is configured to suitably select the support mechanism 90, which is to be raised upright or laid down, in accordance with the size and the like of the inspection object 31. The change of the state between the upright state where the protruding portions 91 are upright and the laid-down state where the protruding portions 91 are laid down may be performed not by means of the driver 90C but by manual operation by an operator.

[Configuration of Controller]

The controller 50 is configured to control components (devices) forming the ultrasonic flaw detector 100. The controller 50 includes: an arithmetic processing unit, such as a microprocessor or a CPU; a storage unit; and an input unit. Through the loading and execution, by the arithmetic processing unit, of a predetermined control program stored in the storage unit, the controller 50 performs various controls of the ultrasonic flaw detector 100.

The storage unit is configured to store various data in a retrievable manner. Examples of the storage unit include known storage devices, such as a memory and a hard disk. The input unit is configured to input, for example, various parameters relating to the control of each component of the ultrasonic flaw detector 100 or other data to the arithmetic processing unit. A known input device, such as a keyboard, a touch panel, a group of push button switches, or the like, serves as the input unit.

It should be noted that the controller 50 may be configured not only as a single controller, but as a group of multiple controllers that operate in cooperation with each other to control the ultrasonic flaw detector 100. Moreover, the controller 50 may be configured as a microcontroller. Furthermore, the controller 50 may be configured as an MPU, PLC (Programmable Logic Controller), logic circuit, or the like.

[Functional Advantages of Ultrasonic Flaw Detector]

The ultrasonic flaw detector 100 according to Embodiment 1 with the above-described configuration can perform inspection of the inspection object 31 in a state where the inspection object 31 is supported by the support mechanism 90, because the ultrasonic wave reflectance increasing or decreasing due to the support mechanism 90 is in a noise-level proportion. Therefore, unlike the conventional art, it is not necessary to move the supported portions of the inspection object from the support mechanism 90 and re-perform flaw detection inspection on these portions. This makes it possible to reduce the work time of the inspection of the inspection object 31.

In the ultrasonic flaw detector 100 according to Embodiment 1, since the support mechanism 90 supports the inspection object 31, even in a case where the flaw detection head 10 scans the inspection object 31 in a manner to contact the inspection object 31 (in a manner to press on the inspection object 31), the inspection object 31 will not bend or warp, and thereby the distance between the inspection object 31 and the probe can be kept constant. This makes precise inspection possible.

From the foregoing description, numerous modifications and other embodiments of the present invention are obvious to a person skilled in the art. Therefore, the foregoing description should be interpreted only as an example and is provided for the purpose of teaching the best mode for carrying out the present invention to a person skilled in the art. The structural and/or functional details can be substantially altered without departing front the spirit of the present invention.

INDUSTRIAL APPLICABILITY

The ultrasonic flaw detector according to the present invention is useful since the ultrasonic flaw detector, which performs inspection of an inspection object while supporting the inspection object by the support mechanism, is capable of greatly reducing the influence of the variation of the reflectance of the ultrasonic wave due to the support mechanism, reducing the work time of the inspection of the inspection object, and performing the inspection precisely.

REFERENCE SIGNS LIST 10 flaw detection head
11 mounting portion
20 calibration area
20 calibration area
21 calibration standard sample
22 artificial defect
30 flaw detection area
31 inspection object
40 moving mechanism
41 moving part
42 gantry part
43A guide member
43B guide member
50 controller 60 container
70 retaining mechanism
71A win member
71B are member
72 driving unit
73 connection part
90 support mechanism
90A supporting member
90B base member
90C driver
91 protruding portion
92 base
93 support
94 rotating portion
94A lower base
94B rod
94C shaft
95 bearing
96 axis
100 ultrasonic flaw detector

The invention claimed is:

1. An ultrasonic flaw detector comprising:
a flaw detection head including a probe that transmits an ultrasonic wave to an inspection object formed by a composite member and receives the ultrasonic wave that has reflected on the inspection object;
a moving mechanism that causes the flaw detection head to perform scanning; and
a support mechanism disposed such that the support mechanism comes into contact with a lower surface of the inspection object, the support mechanism supporting the inspection object, wherein
the support mechanism is configured to come into contact with the inspection object over a predetermined area such that a waveform of the ultrasonic wave that has reflected on a position where the support mechanism is in contact with the inspection object and that is received by the probe is within a noise level,
the support mechanism includes:
a base;
a plurality of protruding portions provided upright on the base and configured such that distal ends of the respective protruding portions come into contact with the lower surface of the inspection object; and
a rotating portion that causes a state of the protruding portions to change between an upright state where the protruding portions are upright and a laid-down state where the protruding portions are laid down, and
the support mechanism is configured to come into contact with the inspection object when the protruding portions are in the upright state, and not to come into contact with the inspection object when the protruding portions are in the laid-down state.

2. The ultrasonic flaw detector according to claim 1, wherein
each of the distal ends of the protruding portions is formed in a tapered shape.

3. The ultrasonic flaw detector according to claim 1, further comprising a retaining mechanism that retains the inspection object.

4. The ultrasonic flaw detector according to claim 3, wherein
the retaining mechanism includes a pair of arm members, and is configured to retain the inspection object by sandwiching, by the pair of arm members, both ends of the inspection object that are not subjected to the scanning.

5. The ultrasonic flaw detector according to claim 2 wherein
the support mechanism further includes a rotating portion that causes a state of the protruding portions to change between an upright state where the protruding portions are upright and a laid-down state where the protruding portions are laid down.

6. The ultrasonic flaw detector according to claim 1, further comprising a retaining mechanism that retains the inspection object.

7. The ultrasonic flaw detector according to claim 2, further comprising a retaining mechanism that retains the inspection object.

8. The ultrasonic flaw detector according to claim 5, further comprising a retaining mechanism that retains the inspection object.

9. The ultrasonic flaw detector according to claim 6, wherein
the retaining mechanism includes a pair of arm members, and is configured to retain the inspection object by sandwiching, by the pair of arm members, both ends of the inspection object that are not subjected to the scanning.

10. The ultrasonic flaw detector according to claim 7, wherein
the retaining mechanism includes a pair of arm members, and is configured to retain the inspection object by sandwiching, by the pair of arm members, both ends of the inspection object that are not subjected to the scanning.

11. The ultrasonic flaw detector according to claim 8, wherein
the retaining mechanism includes a pair of arm members, and is configured to retain the inspection object by sandwiching, by the pair of arm members, both ends of the inspection object that are not subjected to the scanning.

* * * * *